US005521301A

United States Patent [19]
Wallace et al.

[11] Patent Number: 5,521,301
[45] Date of Patent: May 28, 1996

[54] GENOTYPING OF MULTIPLE ALLELE SYSTEMS

[75] Inventors: R. Bruce Wallace, Pasadena; Luis Ugozzoli, Arcadia, both of Calif.

[73] Assignee: City of Hope, Duarte, Calif.

[21] Appl. No.: 678,448

[22] Filed: Apr. 1, 1991

Related U.S. Application Data

[63] Continuation-in-part of Ser. No. 283,142, Dec. 12, 1988, abandoned.

[51] Int. Cl.[6] .............................. C07H 21/04; C12Q 1/68; C12P 19/34
[52] U.S. Cl. ...................... 536/24.33; 435/6; 435/91.2; 935/77; 935/78
[58] Field of Search ............................................. 536/24.33

[56] References Cited

U.S. PATENT DOCUMENTS 5,068,191  11/1991  Clausen et al. ......................... 435/183

OTHER PUBLICATIONS

Mullis et al., Cold Sprng Symp. Quant. Biol. 51: 263–273. (1986).
Sigma Chemical Co. Catalog, p. 938: "Deoxyribonuclic acid, gel electrophoresis markers"(1987).
Wu et al., PNAS (USA) 86: 2757–2760 (Apr. 1989).

Primary Examiner—Stephanie W. Zitomer
Attorney, Agent, or Firm—Edward S. Irons

[57] ABSTRACT

Disclosed is an application of allele specific polymerase chain reaction technology for the direct determination of multiple allele genotyping. ABO genotyping is demonstrated with allele specific primer sets.

2 Claims, 4 Drawing Sheets

GENOTYPING OF MULTIPLE ALLELE SYSTEMS

This invention was made with government support under Grant No. DCB-8515365 awarded by the National Science Foundation. The government has certain rights in the invention.

This application is a continuation-in-part of application Ser. No. 07/283,142 filed Dec. 12, 1988, now abandoned. This application is incorporated herein by reference.

FIELD OF THE INVENTION

The allele-specific polymerase chain reaction (ASPCR) described in application Ser. No. 07/283,142 has proven to be a valuable tool for the detection and analysis of known genetic polymorphisms. This application describes an ASPCR process for genotyping of multiple allele systems such as HLA and ABO. Additional applications of this process include gene mapping, genetic disease diagnosis, paternity testing and forensic science.

BACKGROUND OF THE INVENTION

The ASPCR process described in application Ser. No. 07/283,142 is also set forth in Wu, D. Y., et al., *Proc. Natl. Acad. Sci. USA* 86:2757–2760 (1989). Several groups have used this procedure to achieve allele specific amplifications. See, e.g., Okayama, H., et al. *J.Lab.Clin.Med.* 114:105–113 (1989); Newton, C. R., et al. *Nucleic Acids Res.* 17:2503–2516 (1989); Sarkar, G., et al. *Anal. Biochem.* 186:64–68 (1990).

To achieve allele specificity, PCR is conducted in an allele specific manner such that the presence or absence of an amplified fragment provides direct determination of genotype. Two allele specific oligonucleotide primers, one specific for the sickle cell or other mutant allele and one for the normal allele, together with another primer complementary to both alleles, are used in the PCR with genomic DNA temples. The allele specific primers differ from each other, for example, in their terminal 3' nucleotide. Under the primer annealing temperature and PCR conditions, these primers only direct amplification on their complementary allele.

SUMMARY OF THE INVENTION

This invention provides a novel application of the ASPCR technique used to genotype multiple allele systems. In particular, the invention is useful to determine the ABO genotypes of individuals without the need of family analysis. The method introduces a new strategy for primer design which permits the identification of the different ABO genotypes according to the molecular size of allele specific amplification products. Four primer sets each specific for a different set of ABO alleles are mixed in one reaction and the amplification products resolved on a polyacrylamide gel. Forty one individuals belonging to various families, whose ABO genotype were previously determined serologically, were typed with this new variation of the ASPCR technique. A 100% correlation was found between the serology and ASPCR data. The Mendelian segregation of ABO alleles was also demonstrated in families. The method is rapid, simple, reproducible, and specific. The determination of ABO genotypes is one example of the invention which is useful broadly to determine the genotypes of multiple systems such as HLA and in gene mapping, genetic disease diagnosis, paternity testing and forensic science techniques.

DETAILED DESCRIPTION OF THE INVENTION

This specification describes the application of the invention to the ABO three allele system as a model for its use to genotype other multiple allele systems such as HLA.

The ABO histo-blood group was discovered by Karl Landsteiner in 1900, based on patterns of cross-agglutination observed when red blood cells from certain individuals were mixed with the sera of others. The fact that the ABO antigens were inherited characteristics was shown later by different groups. Epstein, A., et al. *Proc. N.Y. Path. Soc.* 8:117–123 (1908); Dunger, E., et al. *Z. Immun. Forsch.* 6:284–292 (1910); Bernstein, F., *Klin. Wschr.* 3:1495–1497 (1924); Bernstein, F., *Z. indukt. Abstamm. u. VererbLehre* 37:237–270 (1925). The ABO antigens are not confined to red blood cells, they are found in most secretions and tissues of the human body. Race, R., et al., Blood groups in man, Blackwell Scientific Publications (1975). The chemical analysis of these antigens determined that they are oligosaccharides. Watkins, W., Advances in human genetics., Vol. 10, p. 1, Plenum Publishing Corp., New York (1980).

It was found that antigens A and B are derived from H substance which results from the attachment of an L-fucose to a hydrocarbon chain, by the action of two glycosyl transferases. Individuals with blood type A express transferase A ($\alpha 1 \rightarrow 3$N-acetylgalactosaminyltransferase) activity, while individuals with type B express transferase B ($\alpha 1 \rightarrow 3$ galactosyltransferase).

Although the ABO antigens chemical composition, serology, and synthetic pathways became clear many years ago, the molecular basis for the blood types has been determined only recently. The A and B genes, encode the A and B transferases respectively. The two genes differ in only a few nucleotides. These differences change four amino acid residues that are thought to alter the specificity of the A and B transferases. The O gene contains a critical single base deletion, resulting in an inactive protein which is unable to modify the H substance.

The ABO typing is routinely performed using anti-A and anti-B antisera, which are able to distinguish four phenotypes (A, B, AB and O). Without the information which may be given by family analysis, the genotypes AO and AA, and BO and BB are indistinguishable. The known sequences of the three alleles can be used to directly determine the genotypes of an individual. To use this information, however, one must analyze multiple nucleotide positions within the gene. For example, the O allele differs from A and B at nucleotide position 258, but A and B are identical at this position. On the other hand, A and B differ at 4 nucleotide positions, but at all these positions O and A are identical.

ASPCR is a useful method that allows the direct detection of any mutation in genomic DNA by analyzing the PCR products in an agarose or polyacrylamide gel. This invention applies ASPCR to simultaneously determine multiple nucleotide sequences within the glycosyltransferase gene responsible for ABO genotype. This approach allows rapid direct determination of genotype without the need for family studies.

DESCRIPTION OF THE FIGURES

FIG. 1: Overview of ASPCR-ABO genotyping. Primers specific for allele X (P1 and P2) form a stable duplex when genomic DNA from individuals homozygous or heterozygous for allele X is used as DNA template. After 25 rounds of PCR amplification, a fragment will be synthesized with a length which is one nucleotide less than the sum of P1 plus P2. If genomic DNA from individuals homozygous or heterozygous for allele Y is used as DNA template, P1 and P2 will form a mismatched base pair at their respective 3' terminal nucleotide with the variant nucleotide of allele Y. In this case, the amplification will either not proceed or will take place with a reduced efficiency. By controlling the length of the primers, one can produce allele specific amplification products separable by gel electrophoresis.

FIG. 2: ABO genotyping by ASPCR. The figure shows the six major ABO genotypes: OO, BB, OB, AB, OA, and OO. ASPCR-ABO genotyping was performed using genomic DNA from six selected individuals whose genotypes were previously determined by serology. M is a molecular weight marker prepared by ASPCR including all possible fragment lengths that can be produced by the four primer sets and N is a control where all primers were present but no template DNA was added.

FIG. 3: Segregation of the ABO alleles detected by ABO-ASPCR in two families. (a) This family showed the following genotypes: Mother=OB, Sib. 1=AA, Sib. 2=AB, Sib. 3=AB, and Father=OA. (b) In this family the detected genotypes were as follows: Mother=OB, Sib. 1=OO, Sib. 2=OB, Sib. 3=OO, and Father=OO. In each case the genotypes were confirmed by serologic typing. M and N are as in FIG. 2.

EXEMPLIFICATION OF THE INVENTION

Isolation of Genomic DNA

All genomic DNA samples were isolated from peripheral blood obtained from random individuals and selected families. High molecular weight DNA preparation was performed according to a modified procedure using Triton X-100 followed by Proteinase K and RNase treatment. Bell, G. I., et al. *Proc. Natl. Acad. Sci. U.S.A.* 78:5759–5763 (1981). The ABO phenotypes of these individuals were previously determined by serology using anti-A and anti-B antisera.

Chemical Synthesis of Oligonucleotide Primers

ASPCR oligonucleotide primers were synthesized on a Cruachem PS250 DNA synthesizer. Oligonucleotides were purified on a 7M urea 20% polyacrylamide gel. The sequences of the ASPCR primers are shown in Table I.

TABLE I

| Sequences of synthetic oligonucleotide primers | | |
|---|---|---|
| Name | Sequence (5' → 3') | |
| 258-O-1 | TTAAGTGGAAGGATGTCCTCGTGGTA | (SEQ ID NO: 1) |
| 258-O-2 | CATATTTGGGAGCCAGCCAAGGGGTA | (SEQ ID NO: 2) |
| 523-B-1 | CGTGTCAGTGCTGGAGGTGG | (SEQ ID NO: 3) |
| 523-B-2 | TGCCAGCGCTTGTAGGCGCC | (SEQ ID NO: 4) |
| 258-AB-1 | CATATATACGGAAGGATGTCCTCGTGGTG | (SEQ ID NO: 5) |
| 258-AB-2 | ATACATATTTGGGAGCCAGCCAAGGGGTC | (SEQ ID NO: 6) |
| 700-AO-1 | ATGTTTCGGCACCCTGCACCCTG | (SEQ ID NO: 7) |
| 700-AO-2 | GTATGGCTGCTTCCGTAGAAGCC | (SEQ ID NO: 8) |

Polymerase Chain Reaction

All reactions were performed in a volume of 25 µl containing 50 mM KCl, 10 mM Tris-HCl (pH 8.3), 1.5 mM MgCl$_2$, 0.01% (wt/vol) gelatin, 1.25 pmols of primers 523 1B and 523 2B, 1.9 pmols of primers 258 AB-1 and 258 AB-2, 5 pmols of primers 258-O-1 and 258-O-2, 5 pmols of primers 700-AO-1 and 700-AO-2, 50–100 ng of purified template DNA, 2 µM each dATP, dCTP, dGTP and TTP, 0.0132 µM of α[$^{32}$P]dCTP, 3 mM tetramethylammonium chloride (Me$_4$NCl), 2.8% dimethyl sulfoxide (DMSO). 25 µl of mineral oil were added to prevent evaporation. Two units of thermostable *Thermus aquaticus* DNA polymerase (Perkin Elmer, Cetus) were used in each case. Following denaturation of DNA at 95° C. for 5 minutes, the amplification was carried out for 24 cycles as follows: primer annealing and extension at 65° C. for 1 minute, and denaturation at 94° C. for 1 minute. After the last cycle the samples were incubated at 65° C. for 6 minutes and finally at 4° C. until analyzed.

Analysis of PCR Products

An aliquot (2 µl) from each reaction mixture was mixed with 1 µl of 5× Ficoll loading buffer (50 mM Tris-HCl, pH 7.5/5 mM EDTA/0.25% bromophenol blue/0.25% xylene cyanol/15% Ficoll) and subjected to electrophoresis on a 15% polyacrylamide gel. Electrophoresis was performed in 89 mM Tris-HCl/89 mM borate/2 mM EDTA buffer for three hours at 8 watts. After electrophoresis, the gel was transferred to a 3 MM filter paper and then dried for 30 minutes at 80° C. The gel was then exposed to x-ray film with one intensifier screen (Dupont lightening plus) at −80° C. for 2–6 hours.

Experimental Design

The analysis of nucleotide sequences from several cDNA clones encoding the A transferase derived from individuals of blood type O, A, AB, B and unknown showed that there are four nucleotide substitutions between alleles A and B (positions 523, 700, 793, and 800) and a single nucleotide deletion (position 258) in the O allelic form. Yamamoto, F., et al., *J. Biol. Chem.* 265:1146–1151 (1990).

Figure 1:
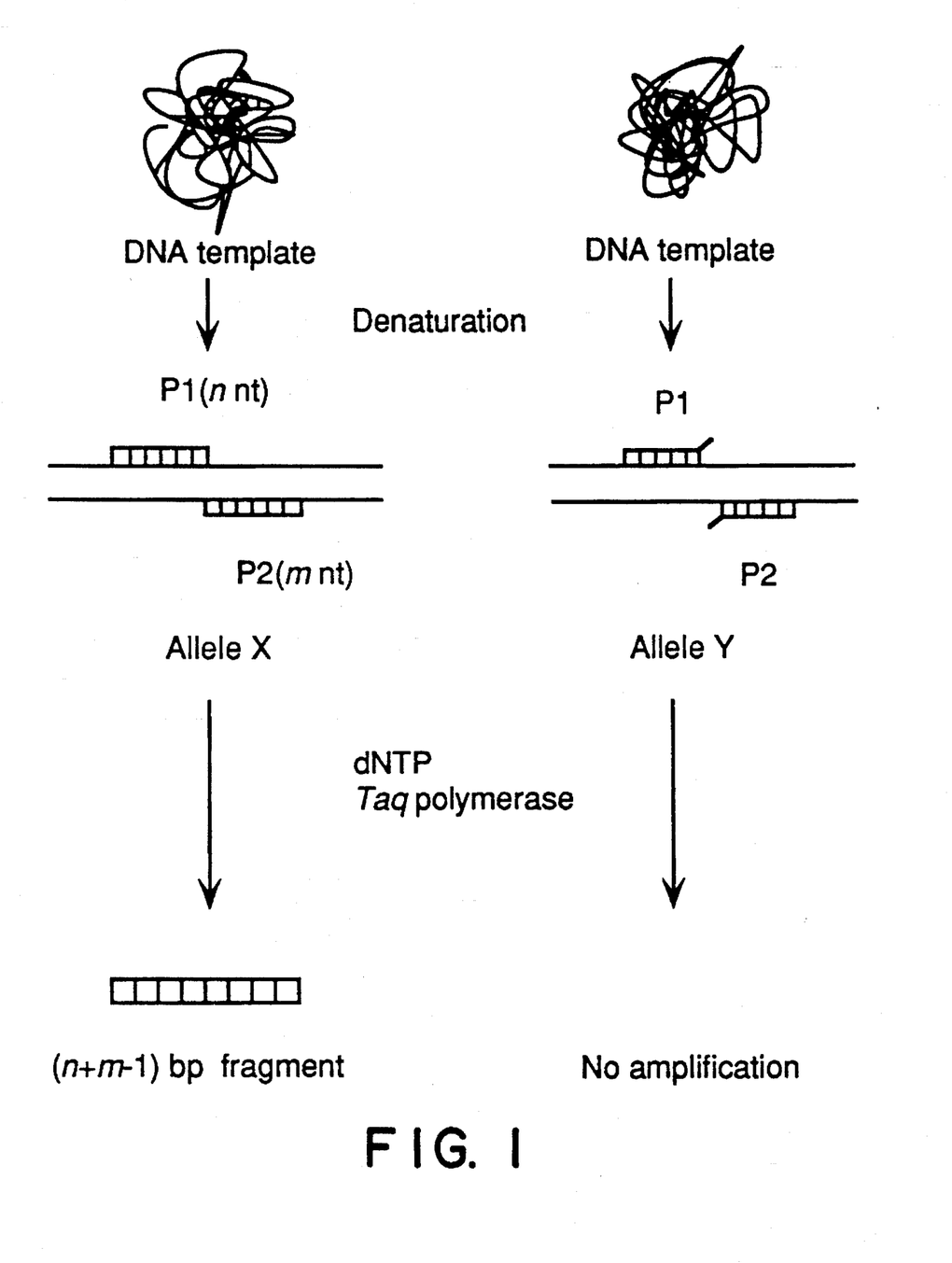

To detect all possible ABO genotypes (OO, AO, AB, BB, OB, and AA), three critical nucleotides positions (258, 523, and 700) were selected in order to design four primer sets. An overview of the strategy used for designing ABO group allele-specific primers is shown in FIG. 1. Both primers corresponding to the selected nucleotide positions were designed to be complementary to both DNA strands with their respective 3' terminal nucleotide forming a matched or mismatched base pair with the variant nucleotide. If the primers form a match with the DNA template at the 3' end, the expected ASPCR fragment will be produced. On the contrary, when the primers form a mismatch with the DNA template at their respective 3' ends, the amplification is blocked or takes place with low efficiency.

Discrimination Between the Different ABO Alleles

To distinguish the different ABO genotypes in one ASPCR reaction, four primer sets were designed (Table I). Both primers of each set have the same length but differ in length from the primers of the other sets (20, 23, 26 and 29 nucleotides long). Thus, the amplification products of the primer sets differ from each other and can be resolved by gel electrophoresis. The eight primers were mixed in one reaction with 50–100 ng of genomic DNA along with the other reagents, and after 25 cycles of ASPCR the products were separated on the basis of their different size on a 15% polyacrylamide gel. Whenever the pairs of primers 258-AB, 258-O, 700-AO, and 523-B hybridized with their specific DNA template and were amplified, they produced a 57, 51, 45, and 39 base pair long ASPCR fragment respectively. A summary of all possible patterns that can be obtained with this ABO-specific ASPCR system is given in Table II.

TABLE II

Pattern of ASPCR fragments for possible all ABO genotypes

| Primer set | Genotype | | | | | |
|---|---|---|---|---|---|---|
| | OO | AO | AA | BO | AB | BB |
| 258-AB | − | + | + | + | + | + |
| 258-O | + | + | − | + | − | − |
| 700-AO | + | + | + | + | + | − |
| 523-B | − | − | − | + | + | + |

+ = Presence of the expected ASPCR fragment.
− = Absence of the expected ASPCR fragment.

The 700 AO primer set was included to discriminate between AB and BB genotypes.

Specificity of the ASPCR-ABO-genotyping

Figure 2:
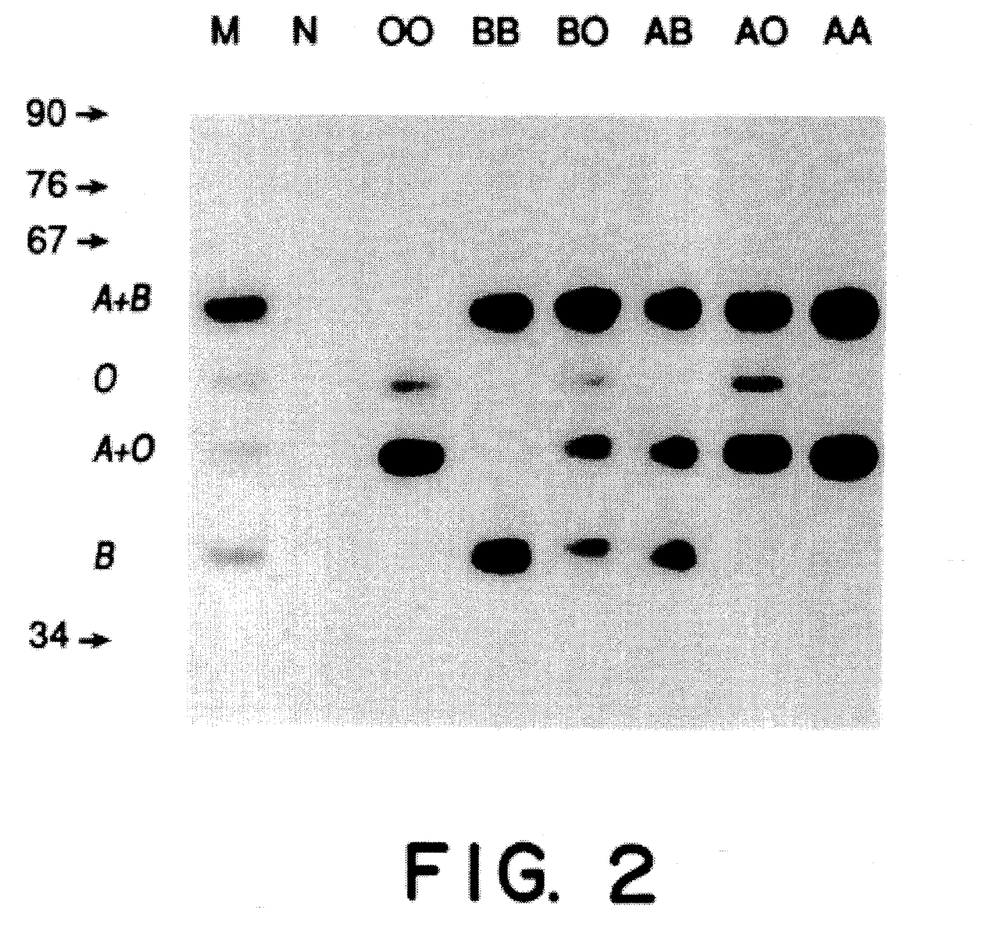

Results in FIG. 2 show the specificity obtained with the ABO-ASPCR genotyping system in six individuals selected from ABO typed families. The six ABO genotypes are clearly distinguishable. A negative control including all the reaction components except the DNA template was performed along with the genotyping reactions. No false positive reactions due to the "primer-dimer" phenomenon were observed using the above described experimental conditions. The inclusion of DMSO in the reaction is of importance to achieve the multiplex ASPCR. It has also been found that TMAC used at a $10^{-3}$M concentration reduces the nonspecific priming elsewhere on genomic DNA. The annealing temperature was also an important parameter to achieve specificity. Low annealing temperatures reduced the reaction specificity due to the synthesis of numerous spurious fragments that made it difficult to interpret the results. A low background level was obtained by labelling the ASPCR fragments with $\alpha$-[$^{32}$P]dCTP.

Family Studies

Figure 3A:
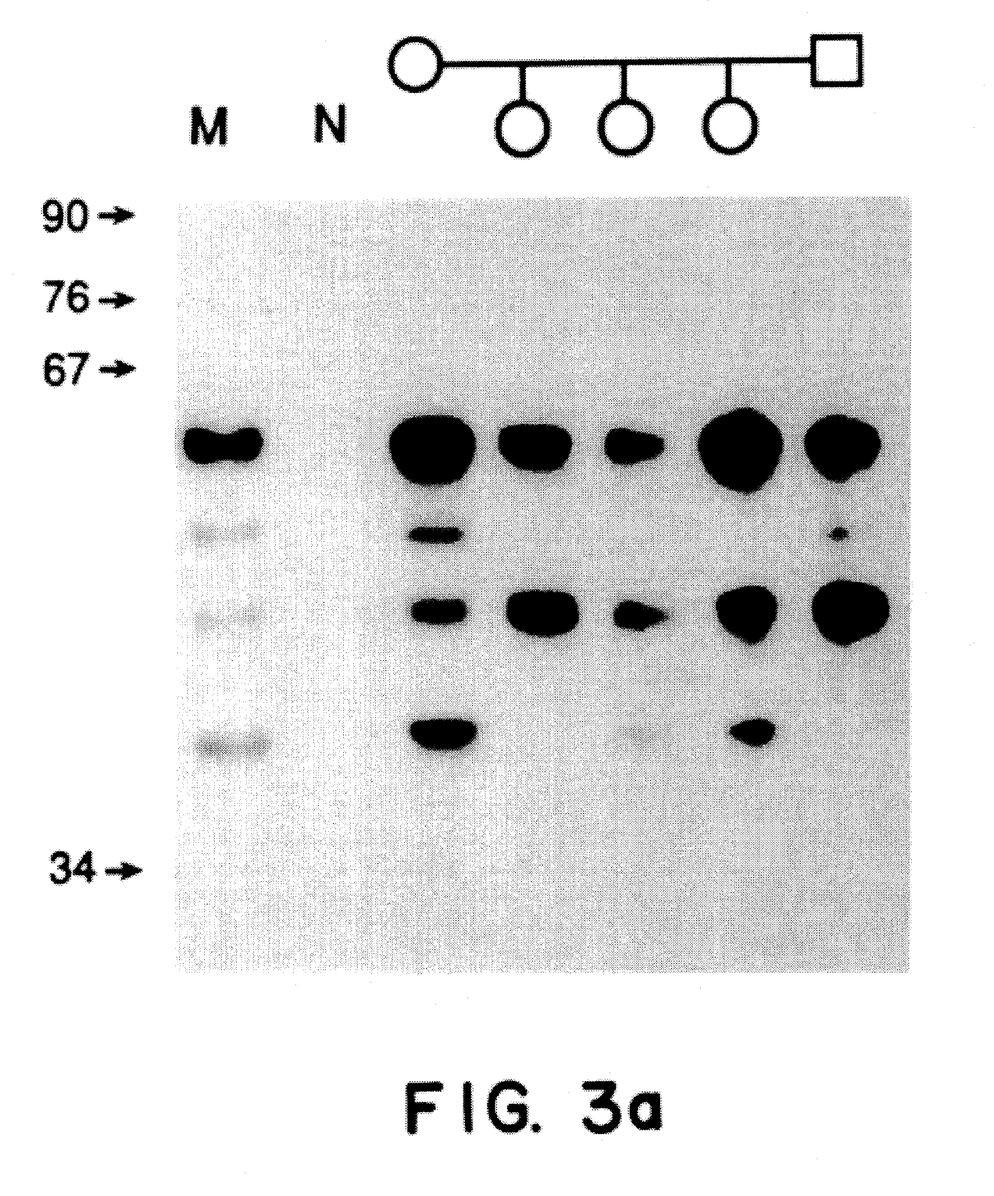
Figure 3B:
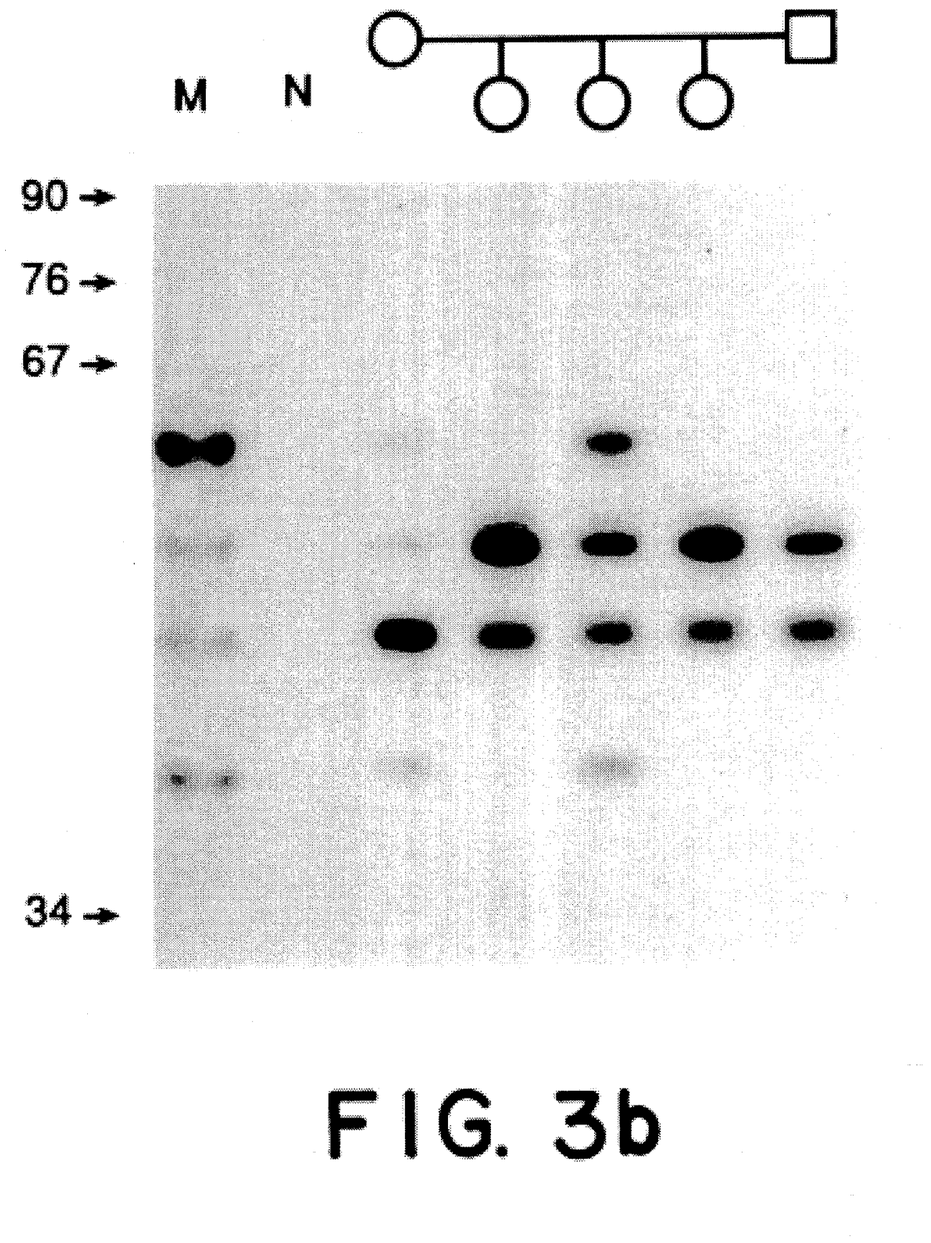

To test the reliability of the ASPCR-ABO genotyping technique, a blind study was performed using genomic DNA isolated from forty-one individuals belonging to different families, whose ABO genotype had been previously determined by serology. A perfect correlation was found in each case between the serology and ASPCR data. Mendelian inheritance of the polymorphic alleles was confirmed in seven families. FIG. 3 (a and b) shows the ABO alleles segregation in two selected families.

DISCUSSION

This invention includes a novel primer design that permits the analysis of the allelic state at one or of several polymorphic loci (situated on the same or different chromosomes) by mixing the primers for each locus in a single PCR reaction. The resulting products are analyzed on a polyacrylamide gel allowing resolution of the amplified products due to their different size.

ASPCR ABO genotyping proved to be rapid (about seven hours), simple (one PCR reaction plus one polyacrylamide gel), sensitive, and specific. Specificity was approached with different strategies. First, the primers specific for allele 1 are designed such that the 3' ends of both primers form mismatches when they hybridize to the DNA template of allele 2. In this case, even if some primer extension can take place, it will be dramatically reduced because of the double mismatch. Under the experimental conditions described in the Exemplification of the Invention section, the mismatches C-C, G-G, T-G, T-C, C-A, G-A, and A-G (template-primer) were all refractory to extension.

To further improve the reaction specificity, 2 µM dNTP concentration was used. The concept of using a dNTP concentration near the $K_m$ value for the enzyme to achieve specificity was suggested by Petruska et al., *Proc. Natl. Acad. Sci. U.S.A.* 85:6252–6256 (1988) and later used in ASPCR by other groups, Li, H., et al. *Proc. Natl. Acad. Sci. U.S.A.* 87:4580–4584 (1990); Ehlen, T., et al. *Biochem. Biophys. Res. Commun.* 160:441–447 (1989).

Two additional problems that could affect specificity were the formation of "primer dimers" and spurious fragments arising from mispriming on similar sequences present elsewhere on genomic DNA. The "primer dimer" is a double strand DNA fragment whose length is approximately the sum of the two primers. It is possibly synthesized by the Taq polymerase when two primers interact at their 3' termini. This phenomenon is observed mainly when the template concentration is very low and when a high number of PCR cycles are used. This phenomenon has not been observed in ASPCR ABO genotyping. The use of TMAC has already been described in oligonucleotides by hybridizations. Wood, W. I., et al., *Proc. Natl. Acad. Sci. U.S.A.* 82:2585–1588 (1985). It eliminates the preferential melting point of A-T versus G-C base pairs, allowing the stringency of the hybridization to be controlled as a function of the probe length. The inclusion of TMAC in ASPCR-ABO reactions dramatically reduced the presence of nonspecific fragments due to mispriming. The intrinsic mechanism by which TMAC has this affect in the ASPCR reactions is not known. Annealing temperature control is important for the reaction specificity. A preferred annealing temperature is from about 60° C. to about 70° C. At the preferred temperature of 65° C., the expected fragments are synthesized at high efficiency and avoid the formation of nonspecific fragments that may complicate the result. Preferably, the primers were titrated in order to find the lowest amount of primer that would produce the expected ASPCR product.

An advantage of this new primer design over the one described in application Ser. No. 283,142 is that all the allelic states are determined in one reaction. The previous primer design involved the performing of one reaction per allele. As the ASPCR-ABO genotyping indicates, this new technique is a valuable methodology that can be reliably applied to gene mapping, genetic disease diagnosis, HLA typing, paternity testing, and forensic science.

We claim:

1. An allele specific polymerase chain reaction primer set for ABO genotyping said primer set comprising SEQ ID NOs: 1 and 2; or SEQ ID NOs: 3 and 4; or SEQ ID NOs: 5 and 6; or SEQ ID NOs: 7 and 8; wherein each of said allele specific primers has the same number of nucleotides;

each of said allele specific primers having been designed to hybridize at specific nucleotide positions on the allele to which it is specific;

said specific nucleotide positions having been selected so that the 3' terminal nucleotide of each of said allele specific primers matches or mismatches a genomic nucleotide critical to an ABO genotype determinant.

2. An allele specific polymerase chain reaction primer system for ABO genotyping, said system comprising four allele specific polymerase chain reaction primer sets; wherein each of said primer sets being allele specific to only one of ABO genotypes OO, AO, AB, AA, BO and BB;

each of said primers of each of said allele specific primer sets having the same number of nucleotides;

the number of nucleotides in each of said primers in each of said allele specific primer sets being different from the number of nucleotides in the primers of any other of said allele specific primer sets;

each of said primers in each of said allele specific primer sets having been designed to hybridize at specific nucleotide positions on the allele to which it is specific;

said specific nucleotide positions having been selected so that the 3' terminal nucleotide of a primer in each of said allele specific primer sets matches or mismatches a genomic nucleotide critical to an ABO genotype determinant;

wherein the allele specific primer sets of said allele specific primer system comprise SEQ ID NOs: 1 and 2; SEQ ID NOs: 3 and 4; SEQ ID NOs: 5 and 6; and SEQ ID NOs: 7 and 8, and wherein concurrent allele specific amplification of a genomic DNA sample with said allele specific primer system yields amplification products of different lengths the patterns of which identify specific ABO genotypes.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
       ( A ) LENGTH: 26
       ( B ) TYPE: Nucleic Acid
       ( C ) STRANDEDNESS: Single
       ( D ) TOPOLOGY: Linear ( i i ) MOLECULE TYPE: Not Applicable ( i i i ) HYPOTHETICAL: No ( i v ) ANTI-SENSE: No ( v ) FRAGMENT TYPE: Not Applicable ( v i ) ORIGINAL SOURCE: Synthically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 1:

TTAAGTGGAA GGATGTCCTC GTGGTA    26

( 2 ) INFORMATION FOR SEQ ID NO: 2:

( i ) SEQUENCE CHARACTERISTICS:
       ( A ) LENGTH: 26
       ( B ) TYPE: Nucleic Acid
       ( C ) STRANDEDNESS: Single
       ( D ) TOPOLOGY: Linear ( i i ) MOLECULE TYPE: Not Applicable ( i i i ) HYPOTHETICAL: No ( i v ) ANTI-SENSE: No ( v ) FRAGMENT TYPE: Not Applicable ( v i ) ORIGINAL SOURCE: Synthically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 2:

CATATTTGGG AGCCAGCCAA GGGGTA    26

( 2 ) INFORMATION FOR SEQ ID NO: 3:

( i ) SEQUENCE CHARACTERISTICS:
       ( A ) LENGTH: 20
       ( B ) TYPE: Nucleic Acid
       ( C ) STRANDEDNESS: Single
       ( D ) TOPOLOGY: Linear ( i i ) MOLECULE TYPE: Not Applicable ( i i i ) HYPOTHETICAL: No ( i v ) ANTI-SENSE: No ( v ) FRAGMENT TYPE: Not Applicable ( v i ) ORIGINAL SOURCE: Synthically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 3:

CGTGTCAGTG CTGGAGGTGG        20

( 2 ) INFORMATION FOR SEQ ID NO: 4:

( i ) SEQUENCE CHARACTERISTICS:
                  ( A ) LENGTH: 20
                  ( B ) TYPE: Nucleic Acid
                  ( C ) STRANDEDNESS: Single
                  ( D ) TOPOLOGY: Linear ( i i ) MOLECULE TYPE: Not Applicable ( i i i ) HYPOTHETICAL: No ( i v ) ANTI-SENSE: No ( v ) FRAGMENT TYPE: Not Applicable ( v i ) ORIGINAL SOURCE: Synthically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 4:

TGCCAGCGCT TGTAGGCGCC        20

( 2 ) INFORMATION FOR SEQ ID NO: 5:

( i ) SEQUENCE CHARACTERISTICS:
                  ( A ) LENGTH: 29
                  ( B ) TYPE: Nucleic Acid
                  ( C ) STRANDEDNESS: Single
                  ( D ) TOPOLOGY: Linear ( i i ) MOLECULE TYPE: Not Applicable ( i i i ) HYPOTHETICAL: No ( i v ) ANTI-SENSE: No ( v ) FRAGMENT TYPE: Not Applicable ( v i ) ORIGINAL SOURCE: Synthically Prepared ( v i i ) IMMEDIATE SOURCE: Synthetically Prepared ( v i i i ) POSITION IN GENOME: None ( i x ) FEATURE: None ( x ) PUBLICATION INFORMATION: None ( x i ) SEQUENCE DESCRIPTION: SEQ ID NO: 5:

CATATATACG GAAGGATGTC CTCGTGGTG 29

(2) INFORMATION FOR SEQ ID NO: 6:

(i) SEQUENCE CHARACTERISTICS:
        (A) LENGTH: 29
        (B) TYPE: Nucleic Acid
        (C) STRANDEDNESS: Single
        (D) TOPOLOGY: Linear     (ii) MOLECULE TYPE: Not Applicable     (iii) HYPOTHETICAL: No     (iv) ANTI-SENSE: No     (v) FRAGMENT TYPE: Not Applicable     (vi) ORIGINAL SOURCE: Synthically Prepared     (vii) IMMEDIATE SOURCE: Synthetically Prepared     (viii) POSITION IN GENOME: None     (ix) FEATURE: None     (x) PUBLICATION INFORMATION: None     (xi) SEQUENCE DESCRIPTION: SEQ ID NO: 6:

ATACATATTT GGGAGCCAGC CAAGGGGTC 29

(2) INFORMATION FOR SEQ ID NO: 7:

(i) SEQUENCE CHARACTERISTICS:
        (A) LENGTH: 23
        (B) TYPE: Nucleic Acid
        (C) STRANDEDNESS: Single
        (D) TOPOLOGY: Linear     (ii) MOLECULE TYPE: Not Applicable     (iii) HYPOTHETICAL: No     (iv) ANTI-SENSE: No     (v) FRAGMENT TYPE: Not Applicable     (vi) ORIGINAL SOURCE: Synthically Prepared     (vii) IMMEDIATE SOURCE: Synthetically Prepared     (viii) POSITION IN GENOME: None     (ix) FEATURE: None     (x) PUBLICATION INFORMATION: None     (xi) SEQUENCE DESCRIPTION: SEQ ID NO: 7:

ATGTTTCGGC ACCCTGCACC CTG 23

(2) INFORMATION FOR SEQ ID NO: 8:

(i) SEQUENCE CHARACTERISTICS:
        (A) LENGTH: 23
        (B) TYPE: Nucleic Acid
        (C) STRANDEDNESS: Single
        (D) TOPOLOGY: Linear     (ii) MOLECULE TYPE: Not Applicable     (iii) HYPOTHETICAL: No     (iv) ANTI-SENSE: No     (v) FRAGMENT TYPE: Not Applicable (vi) ORIGINAL SOURCE: Synthically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 8:

GTATGGCTGC TTCCGTAGAA GCC    23